United States Patent [19]

Carden

[11] 4,041,936
[45] Aug. 16, 1977

[54] BRONCHOSCOPY TUBE

[75] Inventor: Edward Carden, Marina del Rey, Calif.

[73] Assignee: Medical Engineering Corporation, Milwaukee, Wis.

[21] Appl. No.: 570,750

[22] Filed: Apr. 23, 1975

[51] Int. Cl.² .................. A61B 1/06; A61B 17/24; A61M 25/02
[52] U.S. Cl. .................. 128/6; 128/351; 128/349 B
[58] Field of Search .......... 128/6, 351, 10, 11

[56] References Cited

U.S. PATENT DOCUMENTS

| 3,175,557 | 3/1975 | Hammond | 128/351 |
| 3,236,236 | 2/1966 | Hudson | 128/351 X |
| 3,504,676 | 4/1970 | Lomholt | 128/351 |
| 3,731,691 | 5/1973 | Chen | 128/351 |
| 3,734,100 | 5/1973 | Walker et al. | 128/351 |

FOREIGN PATENT DOCUMENTS

| 1,176,320 | 8/1964 | Germany | 128/351 |

Primary Examiner—Channing L. Pace
Attorney, Agent, or Firm—Andrus, Sceales, Starke & Sawall

[57] ABSTRACT

A tube especially useful in fiberoptic bronchoscopy has at one end an adapter which is provided with both means for connection to ventilating means and means for introduction of a fiberoptic bronchoscope and has at the other end a section of reduced external diameter provided with an inflatable cuff.

8 Claims, 3 Drawing Figures

BRONCHOSCOPY TUBE

BACKGROUND OF THE INVENTION

Bronchoscopy, which is the procedure by which the bronchial tree of a patient is visually inspected, is an important technique in the treatment of respiratory failure. However, until quite recently, the procedure frequently was not employed because of the accompanying risk of not being able to maintain adequate ventilation and oxygenation during the procedure. The relatively recent development of the fiberoptic bronchoscope which is flexible and of much smaller external diameter than the conventional bronchoscope has reduced the risks of inadequate ventilation and oxygenation and as a result made the procedure more popular. However, the present practice of introducing the fiberoptic bronchoscope into the bronchial tree of a patient via a conventional endotracheal tube is not without disadvantage. For example, during bronchofiberoscopy, if the bronchofiberscope is introduced through an endotracheal tube, the presence of the bronchofiberscope in the endotracheal tube creates a resistance to flow much higher than is normally encountered. Therefore there is every possibility that the patient may not be able to breathe adequately if awake or be ventilated adequately if under anesthesia or on a ventilator (in an intensive care situation).

SUMMARY OF THE INVENTION

The previously described disadvantages which accompany the use of conventional endotracheal tubes in fiberoptic bronchoscopy are materially overcome by use of the novel bronchoscopy tube of the present invention. In order to minimize the increased resistance to flow which occurs under the described circumstances a special tube has been invented which has a very much lower resistance to flow of gas when the fiberoptic bronchoscope is in place. The tube is made in such a way that the top part of the tubular portion is very wide bore (11 mm. ) and the only narrow part of the tubular portion is that part which goes through the cords. The tubular portion is made of silicone elastomer with a shorter than normal silicone low-pressure cuff. In order to enable the anesthesiologist or physician to ventilate the patient while fiberoptic bronchoscopy is being carried out, a special adapter is provided which has a connection for the bronchoscopy tube, a connection for the anesthesia machine or ventilator, and a silicone cap on the top with a plug in it. When the plug is removed the fiberoptic bronchoscope can be put through the hole in the diaphragm of the cap and advanced down the bronchoscopy tube into the patient's lungs. When the fiberoptic bronchoscope is removed, then the plug can be replaced in the hole in the diaphragm of the cap and the patient ventilated perfectly normally.

THE FIGURES

The detailed description which follows has reference to the following figures:

FIG. 1 which is a perspective view of the bronchoscopy tube of the present invention;

FIG. 2 which is a cross-sectional, enlarged view of the distal end; and

FIG. 3 which is a perspective, exploded view showing the components of the adapter.

DETAILED DESCRIPTION

Figure 1:
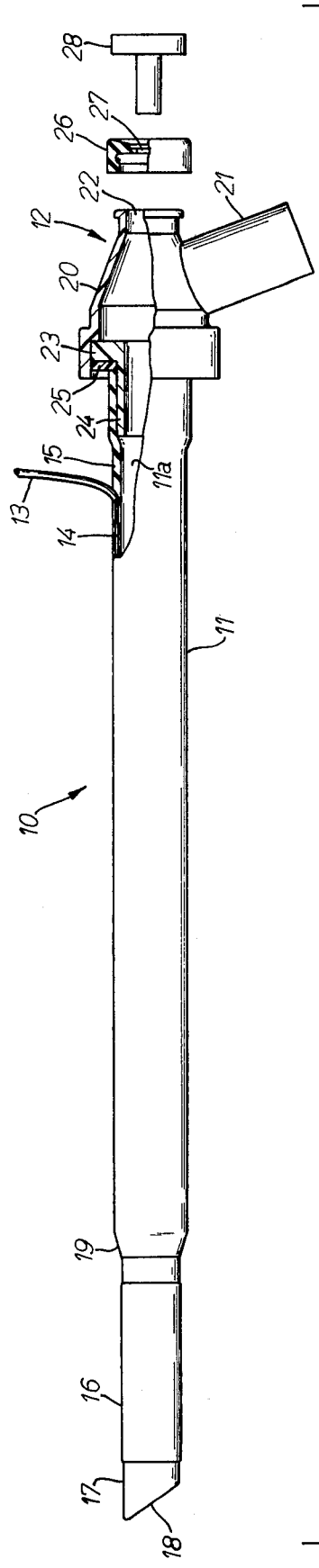

Referring now to the drawings, in FIG. 1 can be seen the tube 10 which is comprised of a tubular member 11 and an adapter 12. The tubular member 11 is formed of a flexible material such as rubber or silicone rubber. At the proximal end of the tubular member 11 (in the right of FIG. 1) is a pilot tube 13 which connects with a cuff inflation lumen 14 in the wall 15 of the tubular member 11. The lumen 14 continues along the length of the tubular member 11 to an opening (not shown) under the cuff 16. The pilot tube 13, the lumen 14, and the opening under the cuff provide the means for introducing fluid into the cuff to inflate it. The cuff can be kept inflated by clamping the pilot tube 13.

In FIG. 1 it can be seen that the tubular member 11 has a major portion of larger diameter and a minor portion 17 of reduced diameter. At the point the major portion of the tubular member 11 and the minor portion 17 of the tubular member meet there is a smooth external shoulder 19 and corresponding internal shoulder. The cuff 16 is positioned about the minor portion 17 which is adjacent the distal end of the tubular member 11 which is diagonally cut to form the tip 18. The edges of the tip 18 may be rounded to minimize tissue trauma.

Figure 2:
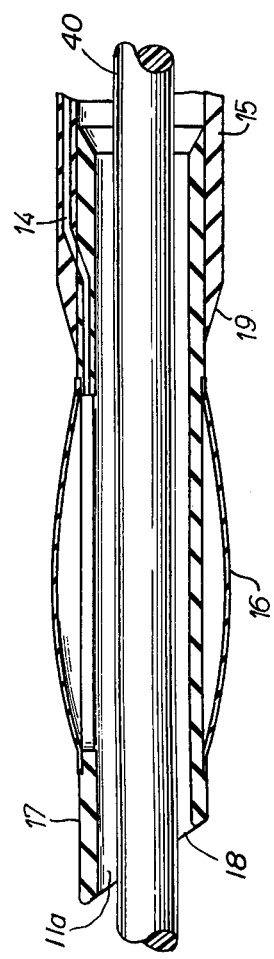

In FIG. 2 can be seen the central passage 11a of the tubular member 11 as well as the lumen 14, the cuff 16, fiberoptic bronchoscope 40 and the shoulder 19. In this figure it can be seen that the central passage in the major portion of the tubular member 11 is larger than that in the minor portion 17.

Figure 3:
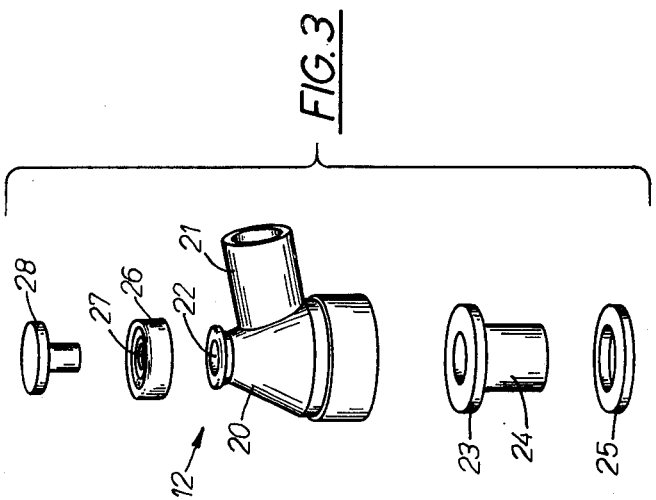

In FIG. 3 is seen an exploded view of the adapter 12. The adapter comprises a conical body portion 20 which is provided with a laterally extending tubular member 21 which is intended for connection to ventilation means (not shown). At the top of the conical body portion 20 there is an aperture 22. The body portion 20 has a cylindrical opening at the bottom and is adapted to receive the flanged ring 23 in such a manner that the flanged ring can freely rotate within the body portion 20. The flanged ring is provided with a dependent skirt 24. The ring retaining member 25 has an internal diameter which is only slightly larger than the external diameter of the cylinder formed by the wall of the dependent skirt 24. The external diameter of the ring retaining member 25 is only slightly smaller than the internal diameter of the cylindrical opening at the bottom of the body portion 20. Thus, when the components of the adapter are aligned as shown in FIG. 3, and the flanged ring 23 is placed in the cylindrical opening of the body portion 20, the ring retaining member 25 is placed about the dependent skirt 24 and then glued or otherwise secured to the internal surface of the bottom opening of the body portion 20 an inexpensive but effective swivel adapter is obtained.

The tube 10 can be assembled as shown in FIG. 1 by forcing the open proximal end of the tubular member 11 over the dependent skirt 24 of the adapter. Or if desired, a piece of rigid tubing can be used as a connector between the adapter 12 and the proximal end of the tubular member 11.

In FIG. 3 there can also be seen the elastic cap 26 which is provided with a central aperture 27 and a plug 28 for closing the aperture 27. The combination of cap and plug serves as an air-tight closure for the aperture 22 in the conical body portion 20 of the adapter 12.

In the preferred practice of the present inventin, the tubular member 11 has an overall length of about 20 cm and is made of silicone rubber. The major portion of the tubular member 11 has an external diameter of about 16 mm and an internal diameter of 11 mm. The minor portion 17 of the tubular member 11 is about 5.5 cm in length and has an external diameter of 11 mm and an internal diameter of about 9.5 mm. The minor portion 17 is long enough to extend past the vocal cords and into the trachea of a normal adult and small enough in external diameter not to cause trauma to the tissue. The cuff 16 of the preferred embodiment is about 2.5 cm long and is of thin silicone rubber material. The preferred adapter is made of clear styrene and has a centrally located aperture 22 which has an internal diameter of 10 mm. The elastic cap 26 is made of rubber or silicone rubber and has a diaphragm-like center provided with an aperture 27 which has a diameter of 4 mm.

The above described preferred bronchoscopy tube is designed for use with a fiberoptic bronchoscope which has an external diameter of 5 mm and a working length of about 56 cm. Generally, such an instrument will have a remotely controllable flexing tip and an internal channel 1 mm in diameter through which solutions may be instilled or secretions aspirated. In practice the tube 10 assembled as shown in FIG. 1 would be placed in the trachea of a patient with the major portion of the tube positioned above the vocal cords and with the minor portion extending through the vocal cords and into the trachea. The cuff would then be inflated and clamped or sealed to keep it inflated. The tube would then be connected to ventilating means via the laterally extending arm 21 of the adapter.

The cap 26 would be positioned about the aperture 22 in the adapter 12 and the fiberoptic bronchoscope threaded through the aperture 27 through the central passage 11a of the tube and into the bronchial tree of the patient. The fiberoptic bronchoscope and cap 26 cooperate to form an air-tight seal and prevent the loss of oxygen or gas to the outside. The tube 10 because of its novel design insures that the patient will receive adequate ventilation and oxygenation.

It will be readily apparent to those skilled in the art that various changes and modifications can be made without departing from the spirit and scope of my invention. For example, the size and dimensions of the components of the tube can be changed or the adapter modified without departing from the gist of my invention. In addition, obvious equivalents can be employed for some of the components I have described and it is may intention that they should be covered by the claims which define by invention.

I claim:

1. A tube for inserting a flexible, elongated, generally cylindrical, fiberoptic bronchoscope through the vocal cords in the larynx while maintaining adequate volumes of gas for ventilating the patient, said tube comprising:
    a tubular body of flexible material having first and second axially aligned sections with a central passage extending from a proximal to a distal end having received within each of said sections bronchoscope, said first section of said tubular body being immediately adjacent the distal end and having an external diameter sufficiently small to permit passage between the vocal cords of the patient and an internal diameter which maximizes clearance with the bronchoscope, said first section being sufficient in length to pass through the larynx into the trachea beyond, said distal end being shaped to provide a smooth tip for ease of insertion, said second section being adjacent said proximal end of said tube and having internal and external diameters greater than those of said first section and sufficiently large to pass gas volumes adequate to ventilate the patient with the bronchoscope in said central passage;
    an expandable, inflatable cuff located on said distal end of said first body section so as to be in the trachea below the larynx when the tube is in use;
    an axially extending inflation lumen disposed contiguous with said tubular body, said inflation lumen communicating with said cuff for permitting inflation of same; and
    an adaptor affixed to the proximal end of said tubular body and communicating with said central passage, said adaptor being provided with means for connection to ventilating gas supply means and an entry port for introducing the bronchoscope into said central passage, said port having means for forming a seal with the bronchoscope.

2. The tube of claim 1 in which the tubular body is made of silicone rubber.

3. The tube of claim 1 wherein said sealing means of said port comprises an elastic annulus formed for embracing the bronchoscope with an interfering fit.

4. The tube of claim 1 in which the adapter is a swivel adapter.

5. The tube of claim 1 in which the internal diameter of said first section of said tubular body is at least as great as the internal diameter of a conventional endotracheal tube capable of passing through the vocal chords of the patient.

6. The tube of claim 1 in which said first section of the tube is about one-fourth the length of the tubular body.

7. The tube of claim 1 in which the internal diameter of said second section of said tubular body is greater than that of a conventional endotracheal tube capable of passing between the vocal chords of the patient.

8. The tube of claim 1 wherein said inflatable cuff is sufficiently small in length as to permit inflation in the trachea below the larynx when the tube is in use.

* * * * *